(12) United States Patent
Farber (10) Patent No.: US 10,156,545 B1
(45) Date of Patent: Dec. 18, 2018

(54) METHOD OF SENSOR CONDITIONING FOR IMPROVING SIGNAL OUTPUT STABILITY FOR MIXED GAS MEASUREMENTS

(71) Applicant: Boris Farber, Solon, OH (US)

(72) Inventor: Boris Farber, Solon, OH (US)

( * ) Notice: Subject to any disclaimer, the term of this patent is extended or adjusted under 35 U.S.C. 154(b) by 88 days.

(21) Appl. No.: 15/077,757

(22) Filed: Mar. 22, 2016

(51) Int. Cl.
*G01N 27/406* (2006.01)
*G01N 27/416* (2006.01)
*G01N 27/407* (2006.01)

(52) U.S. Cl.
CPC ..... *G01N 27/4163* (2013.01); *G01N 27/4067* (2013.01); *G01N 27/4074* (2013.01)

(58) Field of Classification Search
CPC .. G01N 27/4065; G01N 27/409; G01N 27/41; G01N 27/4067
See application file for complete search history.

(56) References Cited

U.S. PATENT DOCUMENTS 6,258,232 B1 * 7/2001 Hasegawa ........... F02D 41/1494
204/424
2005/0284772 A1 * 12/2005 Farber ................ G01N 27/4065
205/775

OTHER PUBLICATIONS

Overview page of "Function Relays, Interfaces and Converters—Coupling Relays and Interfaces", published by Siemens Industry, Inc., revised Mar. 21, 2011.*
"Solid Statements—Solid-State Relays (SSRs) vs Electromechanical Relays (EMRs)", Crydom Inc., Oct. 2010.*

* cited by examiner

*Primary Examiner* — Alexander S. Noguerola
(74) *Attorney, Agent, or Firm* — John D Gugliotta (57) ABSTRACT

An improvement to the pulse discharge technique is suggested by reducing durations of the PDT cycle to less than 0.5 second due to switching hardware modifications and improving the sensor speed of response to less than 1 second. Additional improvement is suggested by utilizing commercial planar lambda sensors and improving planar lambda sensor temperature control tolerance to <+/−0.1° C. by utilizing DC analog PID heater control loop.

4 Claims, 8 Drawing Sheets

FIG. 1

PRIOR ART

PRIOR ART
FIG. 2

PRIOR ART

Figure 3

PRIOR ART

Figure 4

PRIOR ART

Figure 5

PRIOR ART

METHOD OF SENSOR CONDITIONING FOR IMPROVING SIGNAL OUTPUT STABILITY FOR MIXED GAS MEASUREMENTS

BACKGROUND OF THE INVENTION

1. Field of the Invention

The present invention relates generally to an improvement in the present inventor's method or technique, as claimed in the related art, of conditioning a gas sensor through the application of pulse discharges in order to condition mixed-potential gas sensors for detecting gases commonly found in combustion exhaust.

2. Description of the Related Art

Figure 1:
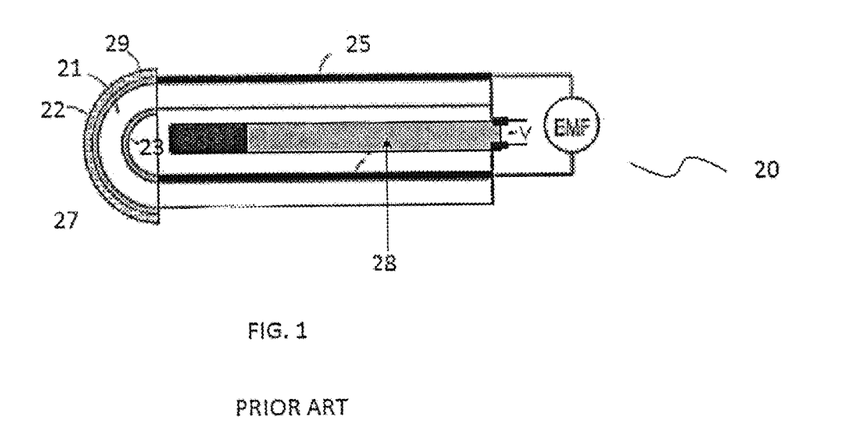
FIG. 1 is a schematic of zirconia oxygen thimble sensor according to the PRIOR ART.
Figure 2:
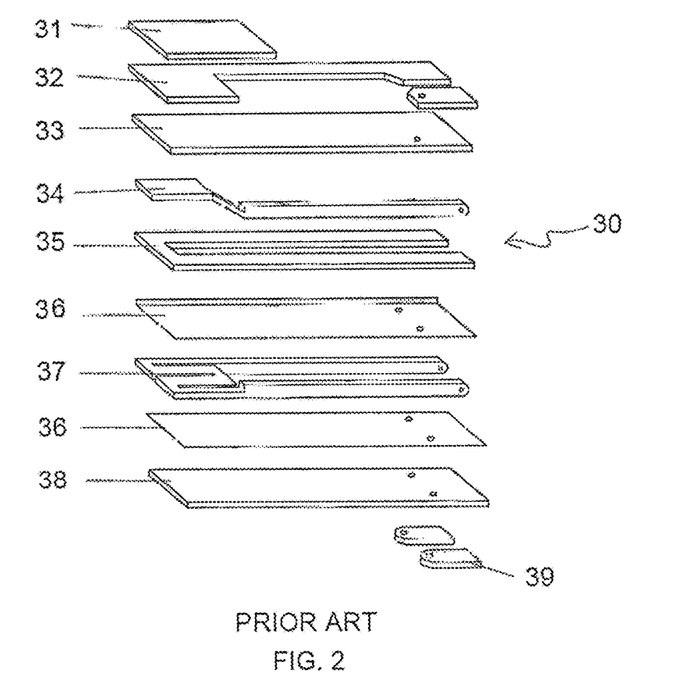
FIG. 2 is a schematic of a commercial zirconia oxygen planar sensor according to the PRIOR ART.

The sensing element used in zirconia oxygen sensors is generally formed of an impermeable zirconia layer separating two porous electrodes, which are typically made of platinum metal. The electrodes are then used to measure the differential oxygen concentration between the measured gas on the outside of the sensor, and a reference gas, usually atmospheric, on the inside of the sensor. By measuring the voltage between two electrodes, the differential oxygen concentration can be calculated. Sensor design has a form of either thimble cell is shown according to the PRIOR ART in FIG. 1. Such a sensor 20 includes a zirconia substrate 21, a measuring electrode 22, a reference electrode 23, connecting leads 24, 25, and a pencil heater 28. The sensor design may further be in stacked planar layers as shown in FIG. 2 according to the PRIOR ART. Such a sensor 30 includes a porous protective layer 31, an external electrode 32, a sensor laminate 33, an internal electrode 34, reference air laminate 35, an insulation layer 36, a heater 37 and a heater laminate 38, with electrical current provided through connection contacts 39. In both cases sensor design include an internal heater to maintain sensor temperature in the desired temperature range.

Figure 3:
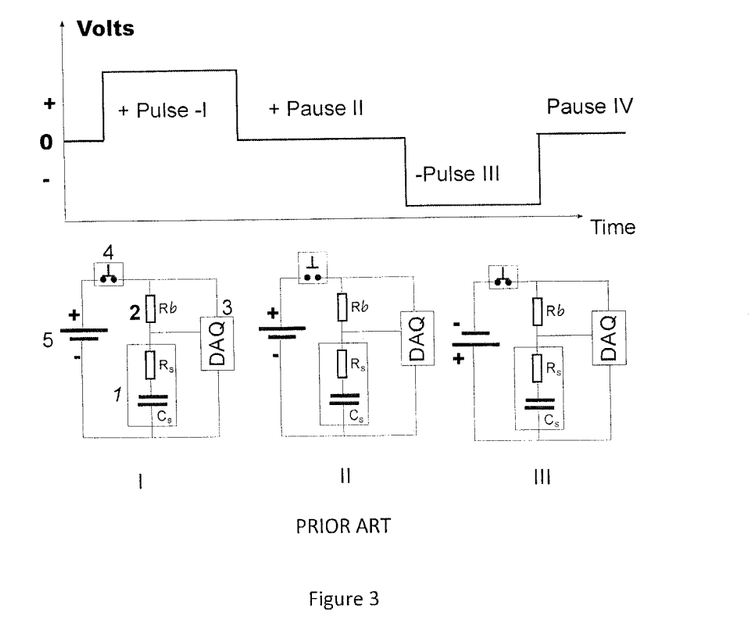
FIG. 3 is a schematic representation of the sensor conditioning in accordance with the PRIOR ART.
Figure 4:
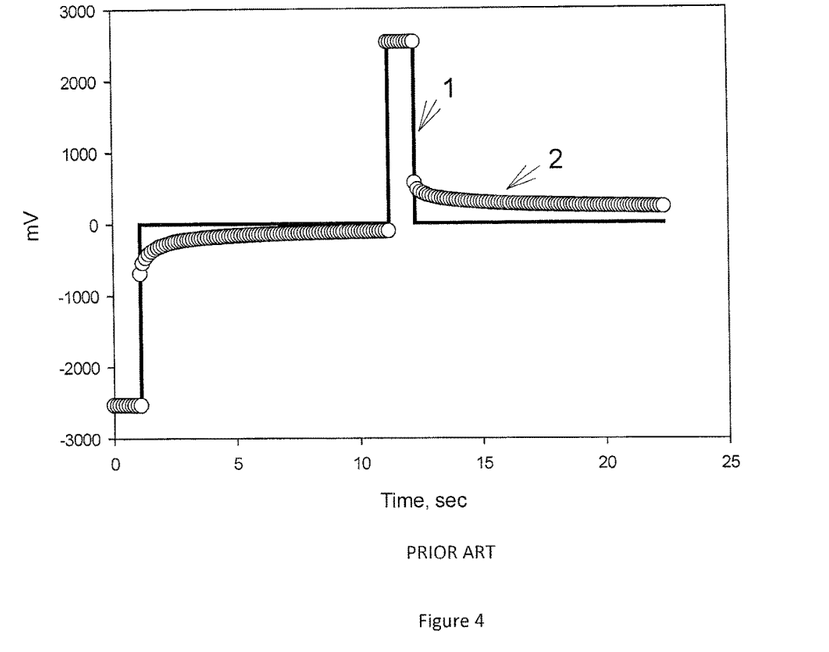
FIG. 4 is applied (1) and measured (2) voltage between sensor electrodes during the Pulse Discharge Technique in accordance with the PRIOR ART.

An improved method for activating such sensors is described in the inventor's own related prior art reflected in U.S. Pat. No. 7,585,402 and recently awarded U.S. Pat. No. 9,304,101. A typical schematic of the pulse discharge technique according to this PRIOR ART is shown in FIG. 3 and described below, which is a representation of the sensor conditioning in accordance with the previous invention. During the charging phases of the Pulse Discharge Technique or PDT (I and III) sensor was connected to the charging power source, during the discharging phases (II and IV) sensor was disconnected from the charging power source and kinetics of the sensor discharge was measured. FIG. 4 further shows applied voltage 41 and measured voltage 42 between the sensor electrodes in accordance with a prior art.

Due to usage of a mechanical relay to disconnect sensor electrodes from the charging power source, duration of the pulses and pauses of the PDT was relatively long ($t_{pulse}$~1 s; $t_{pause}$~5-10 s) which limited speed of the sensor response to ~22 s. To utilize PDT method for measurements of the gas concentration in the engine exhaust a faster speed of response (~1 s) is required.

Additional limitation of the PDT was temperature control algorithm utilized for maintaining required thimble sensor temperature range. This algorithm involved digital PID control loop with a variable duty cycle, the results being shown in conjunction with FIG. 6.

Presently, planar zirconia oxygen sensor became an industry standard due to faster heat-up time. It is desirable to utilize PDT method for a planar sensor design, however, in that a temperature control algorithm utilized previously for thimble cell design does not provide sufficient temperature stability in the range of +/−0.5° C. (see FIG. 5)

SUMMARY OF THE INVENTION

An improvement to the pulse discharge technique is suggested by reducing durations of the PDT cycle to less than 0.5 second due to switching hardware modifications and improving the sensor speed of response to less than 1 second. Additional improvement is suggested by utilizing commercial lambda sensors and improving planar lambda sensor temperature control tolerance to <+/−0.1° C. by utilizing DC analog PID heater control loop.

BRIEF DESCRIPTION OF THE DRAWINGS

The advantages and features of the present invention will become better understood with reference to the following more detailed description and claims taken in conjunction with the accompanying drawings, in which like elements are identified with like symbols, and in which:

DESCRIPTION OF THE PREFERRED EMBODIMENTS

Figure 7:
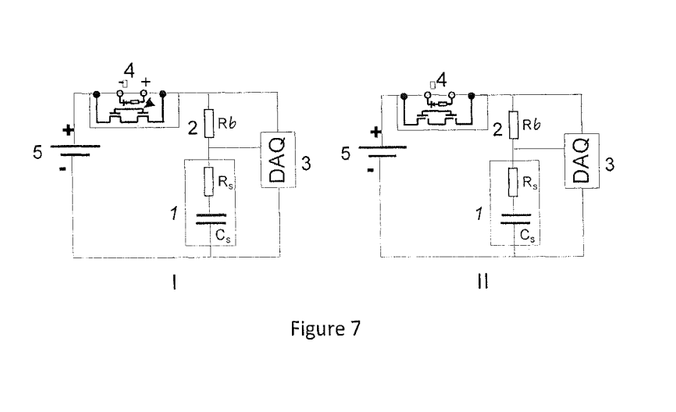
FIG. 7 is a suggested improved diagram according to an exemplary embodiment of the present invention in which the suggested improvement constitute a replacement of a mechanical relay as shown in FIG. 3 position 4 with a solid state relay (position 4), which electronically connect and disconnect sensor with a charging power source.

The best mode for carrying out the invention is presented in terms of its preferred embodiment, herein depicted within the FIGS. 7-13a, in which improvements to the pulse discharge technique are suggested by a replacement of a electro-mechanical relay with a solid state relay, which provide faster and more robust switching of a power supply to and from the sensor electrodes during charging and discharging stages of the PDT as shown in FIG. 7.

Solid state relay or any other electronic device doesn't have moving parts and connection and disconnection of the sensor electrode from the power supply is occurring via variation of the solid state relay resistance in the charging circuit.

Figure 8:
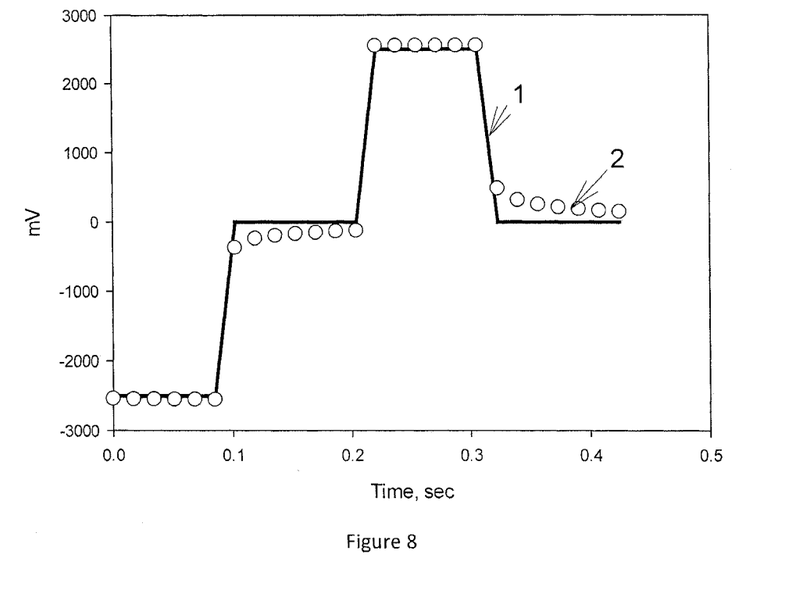
FIG. 8 depicts applied voltage (81) and measured voltage (82) between the sensor's electrodes during the Pulse Discharge Technique with a solid state relays as a switching mechanism.

Additional advantages of the proposed improvements are apparent from FIG. 8. Duration of the PDT cycle is reduced from ~22 seconds in accordance with the PRIOR art to less than 0.5 seconds.

Figure 9:
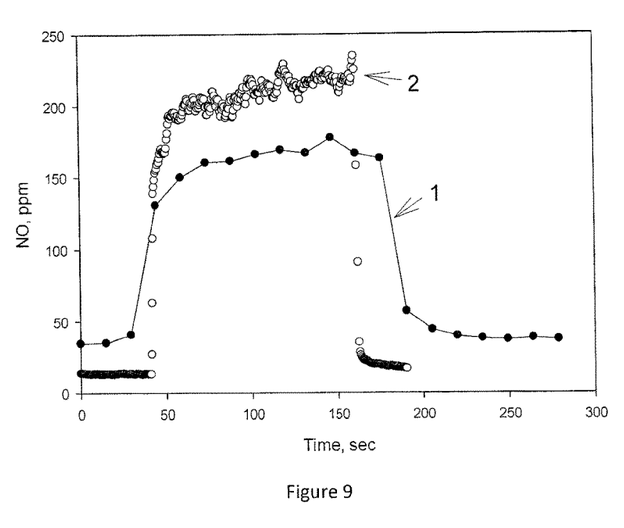
FIG. 9 shows a comparison in the speed of response of an oxygen sensor under conditions of PDT to a step changes in the NO concentration from 0 to 200 ppm.

FIG. 9 shows comparison between measured NO concentration with the zirconia oxygen sensor under condition of PDT in accordance with the PRIOR ART (1) and with a modified electronic circuit, which shows significantly faster response time and more accurate time resolved update rate (2). Measurement update rate was improved from 22 sec to 0.44 sec.

Additional improvements in implementation of the PDT to planar zirconia oxygen sensors are related to modification of the temperature control algorithm. Sensor heater in a commercial planar oxygen sensor is positioned directly underneath the sensor electrodes (see FIG. 2) and the sensor responds very quickly to variations in the applied to the heater voltage. Planar oxygen sensors were developed for the reduction of the light off time. Currently, planar oxygen sensors become industry standard for the air/fuel ratio measurements in an engine exhaust.

Implementation of the PDT method for NOx measurements on a commercial planar oxygen sensors is facing difficulties due to relatively high variations in the controlled sensor temperature in accordance with the PRIOR ART.

Figure 5:
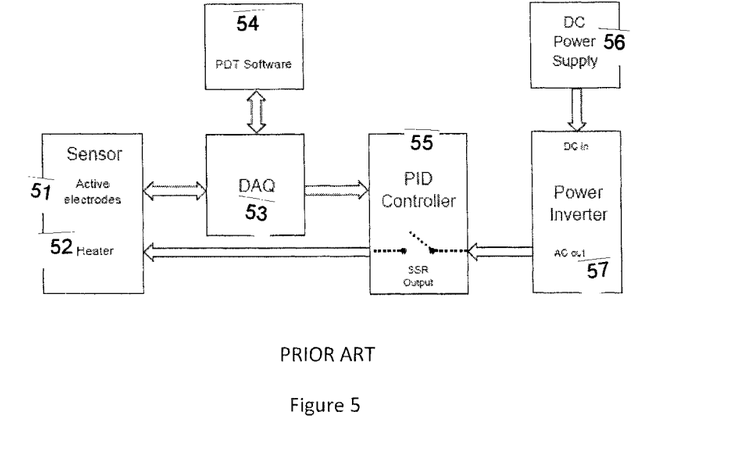
FIG. 5 depicts the temperature stability of a planar zirconia oxygen sensor during the PDT in accordance with the PRIOR ART.
Figure 6:
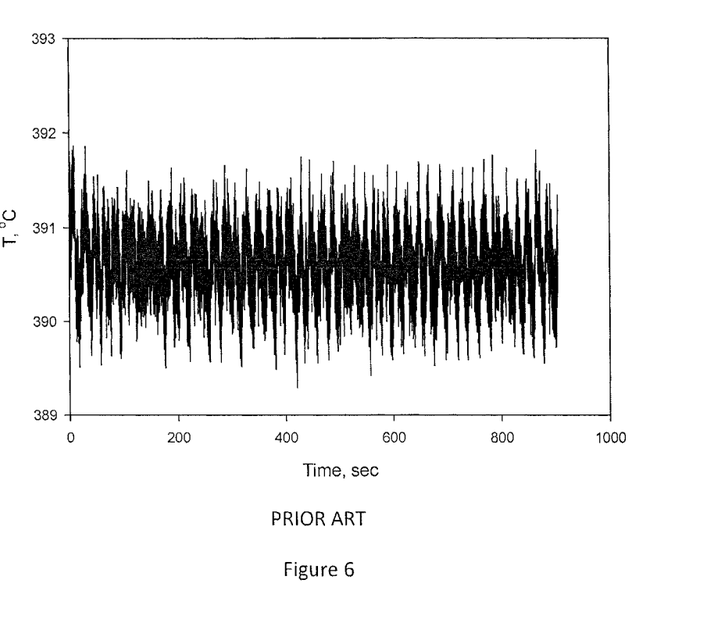
FIG. 6 depicts the temperature control accuracy on a planar oxygen sensor under PDT conditions in accordance with the PRIOR ART.

FIG. 5 shows schematic of the temperature control algorithm. During the charging stages of the PDT, sensor electrodes (51) are connected with the power supply as shown in FIG. 3. Sensor resistance is measured with the Data Acquisition System (DAQ, 53) and converted into analog voltage output of the DAQ. This signal is used as an input of the PID controller (55). PID controller is equipped with a solid state relay, which control AC current (voltage) supplied to the sensor heater (57 and 52). PID controller maintains sensor resistance within pre-defined range by using digital control algorithm with a variable duty cycle of the current (voltage) output to the sensor heater. Sensor resistance is converted to temperature per calibration curve in accordance with PRIOR ART described in U.S. Pat. No. 9,xxx,xxx. Resulting temperature control stability is shown in FIG. 6. Accuracy of the temperature control can be described as +/−0.5° C. As will become apparent these variations in the sensor temperature generate excessive noise in the sensor output and reduce accuracy of the NOx measurements.

Figure 10:
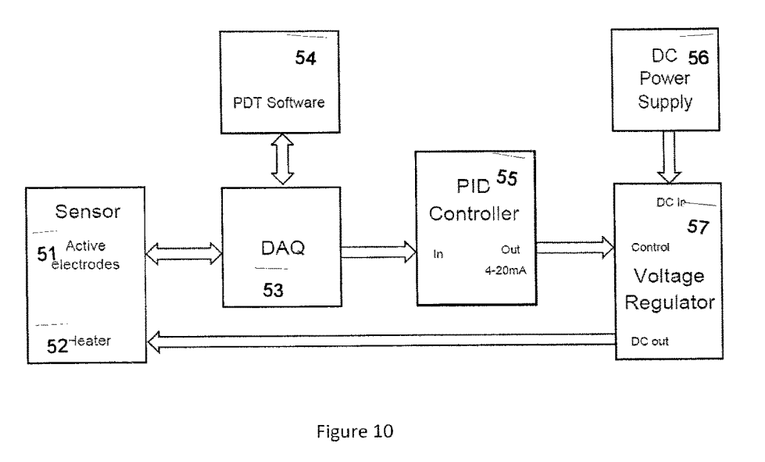
FIG. 10 is a schematic of the control algorithm with the analog PID control loop.
Figure 11:
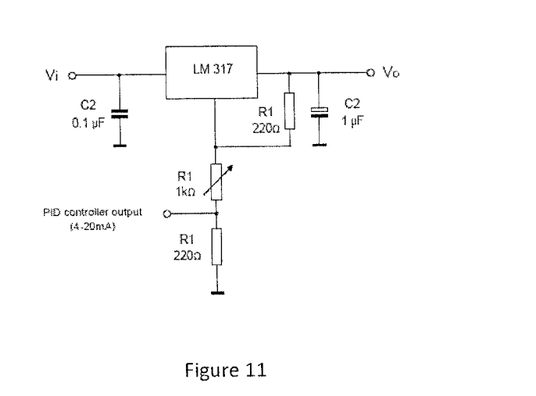
FIG. 11 is a schematic of a linear voltage regulator.

Suggested improvements in the sensor temperature control algorithm is shown in FIG. 10. In the preferred embodiment, PID controller (5) outputs analog signal which is used as an input to the linear DC voltage regulator of the type shown in FIG. 11. DC voltage (current) output is applied to the sensor heater (2, FIG. 10).

Figure 12:
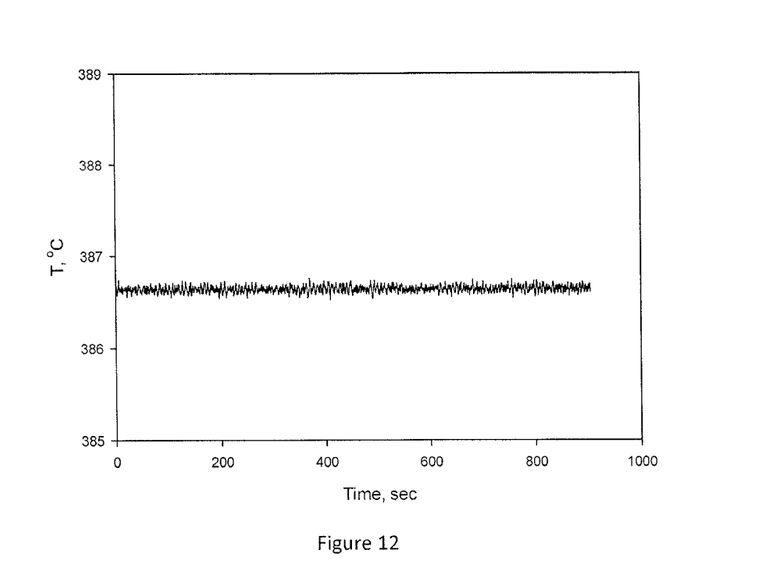
FIG. 12 depicts temperature control stability of a commercial planar oxygen sensor under PDT conditions with an analog voltage PID control.

Since analog voltage control is much faster than a digital control algorithm, resulting temperature control stability is significantly improved as shown in FIG. 12. Accuracy of the sensor temperature control is improved from +/−0.5° C. to +/−0.1° C.

Figure 13:
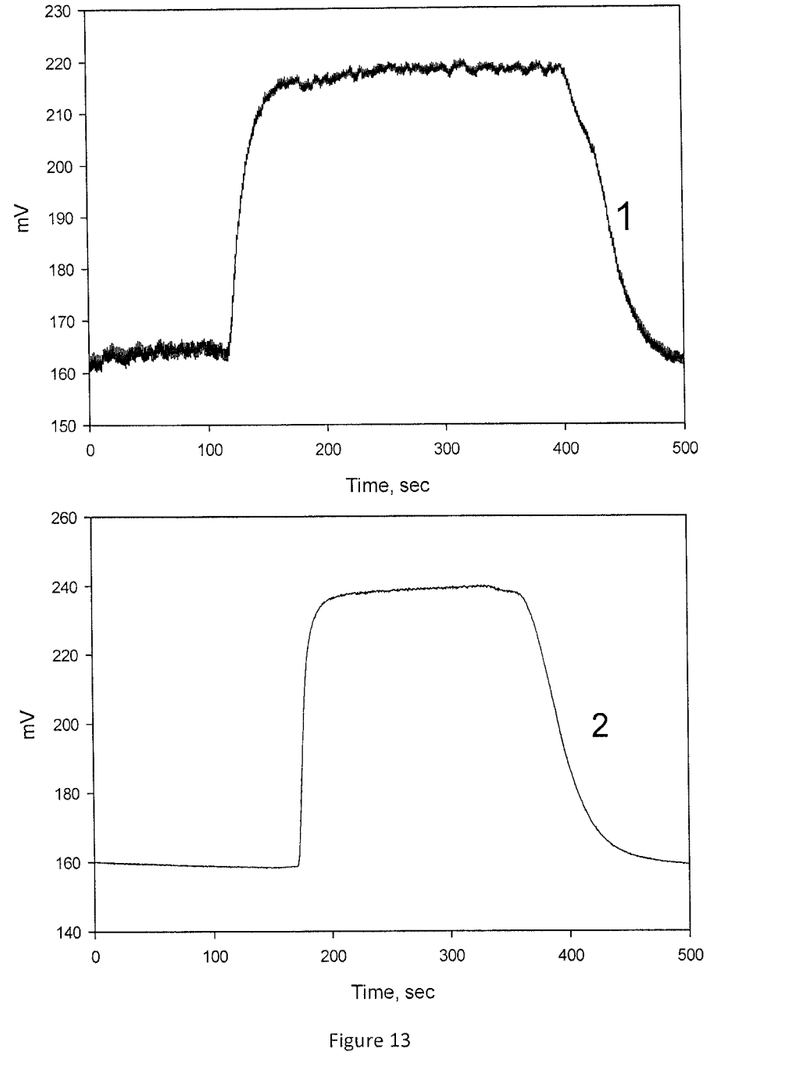
FIG. 13 depicts improvements in the signal to noise ratio during PDT measurements for the improved temperature control algorithm in accordance with the preferred embodiment (2) as compared with the PRIOR ART control algorithm.

As a result of the improved temperature stability of a planar oxygen sensor under condition of PDT, preferred embodiment provides for significantly improved signal to noise ratio during NO measurements. FIG. 13 shows reduction of noise in the sensor output signal in response to the 0-200 ppm changes in NO concentration in the analyzed gas. Preferred embodiment of the analog control algorithm reduced sensor output noise from +/−2 mV to less than +/−0.1 mV.

The foregoing descriptions of specific embodiments of the present invention have been presented for purposes of illustration and description. They are not intended to be exhaustive or to limit the invention to the precise forms disclosed, and obviously many modifications and variations are possible in light of the above teaching. The embodiments were chosen and described in order to best explain the principles of the invention and its practical application, to thereby enable others skilled in the art to best utilize the invention and various embodiments with various modifications as are suited to the particular use contemplated. It is intended that the scope of the invention be defined by the Claims appended hereto and their equivalents. Therefore, the scope of the invention is to be limited only by the following claims.

What is claimed is:

1. A method for controlling the operating characteristics of a gas sensor having at least one member of a thimble or planar shaped solid state ionic conductor supporting at least one pair of metal electrodes and an internal heater, wherein said method comprises:
   a. heating the gas sensor to an elevated temperature by applying current to the internal heater;
   b. continuously measuring the gas sensor's resistance at said elevated temperature; and
   c. monitoring said measured resistance and controlling said sensor's operating temperature within a defined temperature range by controlling current through said internal heater with an analog proportional-integral-derivative (PID) control loop;
wherein applying current to the internal heater is done in fixed positive and negative pulse durations that are selected from a range of between approximately about 0.001 to about 2 seconds.

2. A gas sensor treated with the method of claim 1.

3. The method of claim 1, wherein a fixed pause duration is provided following each of the positive and negative pulses, said fixed pause duration is selected from a range of between approximately 0.001 to approximately 10 seconds.

4. A gas sensor treated with the method of claim 3.

* * * * *